United States Patent
Van Den Nieuwenhuizen et al.

(10) Patent No.: US 9,963,713 B2
(45) Date of Patent: May 8, 2018

(54) BRASSICA PLANTS RESISTANT TO CLUBROOT

(71) Applicant: RIJK ZWAAN ZAADTEELT EN ZAADHANDEL B.V., De Lier (NL)

(72) Inventors: Adrianus Johannes Maria Van Den Nieuwenhuizen, De Lier (NL); Evgeny Novoselov, De Lier (NL); Mathieu Pierre Bertrand Detavernier, De Lier (NL)

(73) Assignee: Rijk Zwaan Zaadteelt En Zaadhandel B.V., De Lier (NL)

( * ) Notice: Subject to any disclaimer, the term of this patent is extended or adjusted under 35 U.S.C. 154(b) by 131 days.

(21) Appl. No.: 14/743,087

(22) Filed: Jun. 18, 2015

(65) Prior Publication Data

US 2015/0284740 A1 Oct. 8, 2015

Related U.S. Application Data

(63) Continuation-in-part of application No. PCT/EP2013/077828, filed on Dec. 20, 2013.

(30) Foreign Application Priority Data

Dec. 21, 2012 (EP) .................................. 12199140

(51) Int. Cl.
| | |
|---|---|
| C12N 15/82 | (2006.01) |
| A01H 5/10 | (2018.01) |
| A01H 1/04 | (2006.01) |
| C12Q 1/68 | (2018.01) |
| A01H 5/00 | (2018.01) |
| A23L 19/00 | (2016.01) |

(52) U.S. Cl.
CPC ........... *C12N 15/8279* (2013.01); *A01H 1/04* (2013.01); *A01H 5/00* (2013.01); *A01H 5/10* (2013.01); *A23L 19/00* (2016.08); *C12Q 1/6895* (2013.01); *A23V 2002/00* (2013.01)

(58) Field of Classification Search
None
See application file for complete search history.

(56) References Cited

U.S. PATENT DOCUMENTS

| 5,955,623 A * | 9/1999 | Grant .................. A01H 5/10 |
| | | 426/601 |
| 8,013,209 B2 | 9/2011 | Linders et al. |
| 2005/0262583 A1 | 11/2005 | Linders et al. |
| 2010/0373343 | 2/2010 | Linders et al. |
| 2011/0231951 A1 | 9/2011 | Linders et al. |

FOREIGN PATENT DOCUMENTS

WO 2004/013334 2/2004

OTHER PUBLICATIONS

Piao et al, 2009, J Plant Growth Regul 28: 252-264.*
Pires et al, Genbank Sequence Accession No. F1762278 published Mar. 11, 2009 attached to the office action.*
Batley and Edwards, 2007, In: Association Mapping in Plants, pp. 95-102.*
International Search Report and Written Opinion of the International Searching Authority dated Mar. 27, 2014, which issued during prosecution of International Application No. PCT/EP2013/077828.
R.E. Voorrips, et al. "Mapping of two genes for resistance to clubroot (*Plasmodiophora brassicae*) in a population of doubled haploid lines of *Brassica oleracea* by means of RFLP and AFLP markers" Theoretical and Applied Genetics; International Journal of Plant Breeding Research, 94(1):1432-2242, Jan. 1997.
K. Nomura, et al. "Evaluation of F-2 and F-3 plants introgressed with QTLs for clubroot resistance in cabbage developed by using Scar markers" Plant Breeding 124(4):371-375, Aug. 2005.
T. Nagaoka, et al. "Identification of QTLs that control clubroot resistance in *Brassica oleracea* and comparative analysis of clubroot resistance genes between *B. rapa* and *B. oleracea*" Theoretical and Applied Genetics; International Journal of Plant Breeding Research, 120(7):1335-1346, Jan. 2010.
J. Rocherieux, et al. "Isolate-specific and broad-spectrum QTLs are involved in the control of clubroot in *Brassica oleracea*" Theoretical and Applied Genetics 108(8):1555-1563, May 2004.
C. Grandclement, et al. "Detection and analysis of QTLs based on RAPD markers for polygenic resistance to Plasmodiophora Brassicae Woron in *Brassica oleracea* L." Theoretical and Applied Genetics 93(1/02):86-90, Jan. 1996.
J.R. Baggett, et al. "Clubroot-resistant Broccoli Breeding Lines OSU CR-2 to OSU CR-8" Hortscience 20 (4):784-785, Jan. 1985.
P. Crisp, et al. "The exploitation of genetic resources of *Brassica oleracea* in breeding for resistance to clubroot (*Plasmodiophora brassicae*)" Euphytica 42(3):215-226, Jan. 1989.

* cited by examiner

*Primary Examiner* — Elizabeth F McElwain
(74) *Attorney, Agent, or Firm* — Vedder Price P.C.; Thomas J. Kowalski; Deborah L. Lu (57) ABSTRACT

The present invention relates to a *Brassica* plant, in particular a *Brassica oleracea* plant carrying a genetic determinant that may comprise QTLI and/or QTL2 and/or QTL3, which confer resistance against *Plasrnodiophora brassicae*, and which genetic determinant is present in plants that are grown from seeds which were deposited with the NCIMB under NCIMB accession number 41851. The present invention further relates to a nucleic acid molecule causative of resistance against *Plasrnodiophora brassicae*, which may comprise a DNA sequence, located on chromosome 3, a nucleic acid molecule causative of resistance against *Plasrnodiophora brassicae*, which may comprise a DNA sequence located on chromosome 8, and a nucleic acid molecule causative of resistance against *Plasrnodiophora brassicae*, which may comprise a DNA sequence, located on chromosome 4.

15 Claims, 1 Drawing Sheet
(1 of 1 Drawing Sheet(s) Filed in Color)

SEQUENCE LISTING

<160> NUMBER OF SEQ ID NOS: 15

<210> SEQ ID NO 1
<211> LENGTH: 80
<212> TYPE: DNA
<213> ORGANISM: Brassica oleracea
<220> FEATURE:
<221> NAME/KEY: source
<222> LOCATION: 1..80
<223> OTHER INFORMATION: /organism="Brassica oleracea"
/mol_type="unassigned DNA"

<400> SEQUENCE: 1
acagagtctt caaacatttc atagcacgaa gctgagttgc tagtgtggtt tcaggtgctg 60
ctactaacat tgttgggatg 80

<210> SEQ ID NO 2
<211> LENGTH: 79
<212> TYPE: DNA
<213> ORGANISM: Brassica oleracea
<220> FEATURE:
<221> NAME/KEY: source
<222> LOCATION: 1..79
<223> OTHER INFORMATION: /organism="Brassica oleracea"
/mol_type="unassigned DNA"

<400> SEQUENCE: 2
gttagtctca tagtttacat acatactctg ctggtaatac tcatgggacg ttggtgctga 60
gtccatcacg accgtgttg 79

<210> SEQ ID NO 3
<211> LENGTH: 80
<212> TYPE: DNA
<213> ORGANISM: Brassica oleracea
<220> FEATURE:
<221> NAME/KEY: source
<222> LOCATION: 1..80
<223> OTHER INFORMATION: /organism="Brassica oleracea"
/mol_type="unassigned DNA"

<400> SEQUENCE: 3
tcagattctc tgaagtcaat cttgtgttca acaccagctt tgtttataat tggcaatcct 60
acctcttcgt atgagcctct 80

<210> SEQ ID NO 4
<211> LENGTH: 79
<212> TYPE: DNA
<213> ORGANISM: Brassica oleracea
<220> FEATURE:
<221> NAME/KEY: source
<222> LOCATION: 1..79
<223> OTHER INFORMATION: /organism="Brassica oleracea"
/mol_type="unassigned DNA"

<400> SEQUENCE: 4
atcatcttcc atagctttca catgctttgt ggctcccacg ctcactccag ttctgagaac 60
ttgcgtaacc aacttctcg 79

-continued

```
<210> SEQ ID NO 5
<211> LENGTH: 79
<212> TYPE: DNA
<213> ORGANISM: Brassica oleracea
<220> FEATURE:
<221> NAME/KEY: source
<222> LOCATION: 1..79
<223> OTHER INFORMATION: /organism="Brassica oleracea"
      /mol_type="unassigned DNA"

<400> SEQUENCE: 5
ctgcttccct ttcccaaaca aacctccaaa ccaagayccc gaacctgcct ccgaagcaga    60
tgaagtctcc ggcacaggc                                                79

<210> SEQ ID NO 6
<211> LENGTH: 79
<212> TYPE: DNA
<213> ORGANISM: Brassica oleracea
<220> FEATURE:
<221> NAME/KEY: source
<222> LOCATION: 1..79
<223> OTHER INFORMATION: /organism="Brassica oleracea"
      /mol_type="unassigned DNA"

<400> SEQUENCE: 6
aatgagcgag gacgtgagcg ggaacaagtt cttcgacgag gcaatgatgg tggagctagc    60
gcagcagacg ggtgatctg                                                79

<210> SEQ ID NO 7
<211> LENGTH: 79
<212> TYPE: DNA
<213> ORGANISM: Brassica oleracea
<220> FEATURE:
<221> NAME/KEY: source
<222> LOCATION: 1..79
<223> OTHER INFORMATION: /organism="Brassica oleracea"
      /mol_type="unassigned DNA"

<400> SEQUENCE: 7
ggactagatt ggaatagtaa cctaaatgaa gcaatggagg atgataaaga agaagttgtt    60
ggggctgcgc aggtcgaga                                                79

<210> SEQ ID NO 8
<211> LENGTH: 79
<212> TYPE: DNA
<213> ORGANISM: Brassica oleracea
<220> FEATURE:
<221> NAME/KEY: source
<222> LOCATION: 1..79
<223> OTHER INFORMATION: /organism="Brassica oleracea"
      /mol_type="unassigned DNA"

<400> SEQUENCE: 8
gatwgggtca tccgaatcca cacatcctwc agcacctatc ttctactaag tctatcgtca    60
taaataagag atccaragg                                                79

<210> SEQ ID NO 9
<211> LENGTH: 80
<212> TYPE: DNA
<213> ORGANISM: Brassica oleracea
<220> FEATURE:
<221> NAME/KEY: source
<222> LOCATION: 1..80
<223> OTHER INFORMATION: /organism="Brassica oleracea"
      /mol_type="unassigned DNA"

<400> SEQUENCE: 9
```
agaggtccgt ggaatcccat cttactggat cgacagtgag caacggatag gacctgggaa    60
caaaatagcc tataagctcc                                                80

<210> SEQ ID NO 10
<211> LENGTH: 80
<212> TYPE: DNA
<213> ORGANISM: Brassica oleracea
<220> FEATURE:
<221> NAME/KEY: source
<222> LOCATION: 1..80
<223> OTHER INFORMATION: /organism="Brassica oleracea"
      /mol_type="unassigned DNA"

<400> SEQUENCE: 10
gatgtcggtg tagagacctg gacctttcac cattttttgct ttgctttgct tmctaccama    60
aagaacaaaa gatacctcga                                                80

<210> SEQ ID NO 11
<211> LENGTH: 79
<212> TYPE: DNA
<213> ORGANISM: Brassica oleracea
<220> FEATURE:
<221> NAME/KEY: source
<222> LOCATION: 1..79
<223> OTHER INFORMATION: /organism="Brassica oleracea"
      /mol_type="unassigned DNA"

<400> SEQUENCE: 11
agcttggagc tagagcggag gagatgcgca ggaagctagt aggatcagtg acagaaggca    60
gctcttttgc tgatttaga                                                 79

<210> SEQ ID NO 12
<211> LENGTH: 79
<212> TYPE: DNA
<213> ORGANISM: Brassica oleracea
<220> FEATURE:
<221> NAME/KEY: source
<222> LOCATION: 1..79
<223> OTHER INFORMATION: /organism="Brassica oleracea"
      /mol_type="unassigned DNA"

<400> SEQUENCE: 12
ccactgatga gcgaaggcat aagcyarggc tctttcccgc ttgatcgttg cttcttccct    60
ttgatgtatc ctcccyaag                                                 79

<210> SEQ ID NO 13
<211> LENGTH: 80
<212> TYPE: DNA
<213> ORGANISM: Brassica oleracea
<220> FEATURE:
<221> NAME/KEY: source
<222> LOCATION: 1..80
<223> OTHER INFORMATION: /organism="Brassica oleracea"
      /mol_type="unassigned DNA"

<400> SEQUENCE: 13
ggacacttaa aaaacccct tgctctcttc aatagcgtta taaagcaaat cagctttcct    60
ctgattcttc ctctccactt                                                80

<210> SEQ ID NO 14
<211> LENGTH: 80
<212> TYPE: DNA
<213> ORGANISM: Brassica oleracea
<220> FEATURE:

```
<221> NAME/KEY: source
<222> LOCATION: 1..80
<223> OTHER INFORMATION: /organism="Brassica oleracea"
      /mol_type="unassigned DNA"

<400> SEQUENCE: 14
ggagaaatga agcggaaagt aaaaacacac acacagattg agtttttttt cgttttactt      60
ttttctgttt ttttttttct                                                 80

<210> SEQ ID NO 15
<211> LENGTH: 80
<212> TYPE: DNA
<213> ORGANISM: Brassica oleracea
<220> FEATURE:
<221> NAME/KEY: source
<222> LOCATION: 1..80
<223> OTHER INFORMATION: /organism="Brassica oleracea"
      /mol_type="unassigned DNA"

<400> SEQUENCE: 15
ctcggctctt ttgttggaga gatacgaagg tggcggagat ctaccagcgg cgggatgagg      60
aggggtcgcc ggattgctct                                                 80
```

BRASSICA PLANTS RESISTANT TO CLUBROOT

RELATED APPLICATIONS AND INCORPORATION BY REFERENCE

This application is a continuation-in-part application of international patent application Serial No. PCT/EP2013/077828 filed 20 Dec. 2013, which published as PCT Publication No. WO 2014/096415 on 26 Jun. 2014, which claims benefit of European patent application Serial No. 12199140.0 filed 21 Dec. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Jun. 17, 2015, is named 43104002194_SL.txt and is 5,159 bytes in size.

FIELD OF THE INVENTION

The present invention relates to *Brassica oleracea* plants resistant to clubroot. The invention further relates to parts of these plants, to seeds and to other propagation material, and to the progeny of these plants.

BACKGROUND OF THE INVENTION

*Brassica* is a genus of plants, taxonomically embedded within the Brassicaceae family. It contains many economic important crops that serve as a source of food, but species are also employed in the production of oil. In general, the *Brassica* genus includes *B. napus*, *B. nigra*, *B. rapa*, *B. juncea* and *B. oleracea*. *Brassica napus* is very important in the production of vegetable oil that is increasingly applied in the fuel industry. Together with *Brassica rapa*, *Brassica nigra* and *Brassica juncea*, *Brassica oleracea* is a species that plays a very important role in the production of human food. Over time, cultivars originated within *B. oleracea* amongst which cabbage, Chinese cabbage, cauliflower, collards, broccoli, kohlrabi and Brussels sprouts can be found.

The wild cabbage has been bred into a broad range of different horticultural cultivars that remained sexually compatible. However, their appearance does not show a very high level of phylogenetic similarity. The wide range in differences of morphological characteristics within *Brassica oleracea* has long been of interest and form the foundation of a cultivars' uniqueness. These include an enlarged inflorescence (cauliflower, broccoli); an enlarged stem (kohlrabi); an enlarged apical bud (cabbage); enlarged lateral buds (Brussels' sprouts).

Breeding of cruciferous vegetables like *Brassica oleracea* varieties aims at the production of commercial varieties optimally adapted to local growing conditions which allows the grower to maximize the productivity of high quality plants. Many characteristics need to be taken into account during selection which relate to both input as well as output traits. One of the most important input traits in this respect relates to disease resistance, in particular to resistance towards micro-organisms.

Cabbage plants are affected by a wide range of pests and diseases. These threats are therefore high priority objects for cabbage breeders, in order to obtain crops that are vigorous and highly resistant. In absence of resistances in these crops, growers necessarily have to apply agronomic strategies like crop rotation and intercropping in order to reduce pest damage in areas where cruciferous vegetables are grown.

Clubroot is a common, probably the most damaging disease found among cabbages, radishes, turnips and other plants belonging to the Crucifereae family. It is caused by the eukaryotic unicellular organism *Plasmodiophora brassicae* Wor. The incidence of clubroot in North West Europe, Japan, North America and Australia is estimated to affect around 10% of grown *B. oleracea* crops. The disseminated spores remain infectious for 15 years. Through addition of calcium and other means to prevent a drop op pH of the soil, the disease pressure may be reduced. Chemical treatment is considered to be ineffective due to environmental regulations or these chemicals are too expensive.

The life cycle of the parasite consists of two main phases. The first phase takes place in the vicinity of root hairs. After germination of the resting spore, the primary zoospore becomes attached to a root hair. By turgor pressure from the spore cyst, a small, wall-less amoeba is injected in the cytoplasm of the host and a primary, multinucleate plasmodium is formed. Through mechanisms of phagocytosis, plasmodia migrate deeper into the root tissue and reach the root cortex. In this second phase, the multinuclear secondary plasmodium will develop and through cell divisions and hypertrophy, gall formation is triggered. Finally, host cells will contain haploid, resisting spores which can be disseminated.

The clubs formed on the roots inhibit the transport of nutrients and water, leading to inhibition of plant growth and an increase of the susceptibility to wilting. Infection by *Plasmodiophora brassicae* occurs worldwide and it has an extensive host range. Cultural practices and/or chemical treatments have been unsuccessful in protecting crops or have proven to be too expensive. Therefore, the development of resistant cultivars is now considered the most economical and efficient method for the control of clubroot.

However, multiple isolates of *Plasmodiophora brassicae* exist. This makes breeding of different cultivars of different *Brassica oleracea* cultivars complex, as different cultivars are infected by different isolates of *P. brassicae*. Also, field populations of *P. brassicae* exhibit clear differences in pathogenicity. These populations can be classified with respect to differential pathogenicity. The differential series as classified by Williams (1966) and the European Clubroot Differential set (ECD) by Buczacki are commonly used.

Several genetic sources of resistance have already been described in literature. These relate to monogenic as well as polygenic and recessive as well as dominant types. In general, the monogenic dominant resistances are identified in *B. rapa* and *B. napus*. In *B. oleracea*, in general only polygenic recessive sources have been found. These resistances did not show to be sufficiently resistant to clubroot races and secondly, it has been shown very difficult to transfer the resistance between commercial *B. oleracea* lines. The transfer of a resistance from *B. rapa* to *B. oleracea* has also been shown to be difficult, as the sexual compatibility species of these *Brassica* species is low.

Resistances to *Plasmodiophora brassicae* have been identified. However, several arguments are relevant when considering the present invention in the light of the prior art. Firstly, it is important that resistance against *Plasmodiophora brassicae* is as broad as possible. A broader resistance will provide longer protection, especially in view of the virulent and persistent character of the pathogen causing clubbed roots.

Secondly, the genetic background of the resistance is of important relevance in two ways. On the one hand, it is an advantage when the genetic basis is limited to a small number of genes, preferably one gene. This enables easy transfer of the genetic determinant(s) conferring the resistance to other *Brassica* plants. On the other hand, with regard to complex genetic relations found within the *Brassica* genus, it is also an advantage if the genetic determinant(s) conferring the resistance is derived from the same *Brassica* species, e.g. *Brassica oleracea*.

Citation or identification of any document in this application is not an admission that such document is available as prior art to the present invention.

SUMMARY OF THE INVENTION

The present invention relates to the species within *Brassica oleracea* that are affected by infection with clubroot.

Summarizing, there is a need for a reliable resistance towards multiple strains of clubroot that is also easy to transfer between commercial *Brassica* crops, in particular, *Brassica oleracea* crops.

It is the object of the present invention to improve *Brassica* plants, in particular *Brassica oleracea* plants with respect to resistance to multiple strains of *Plasmodiophora brassicae* (clubroot) wherein the genetic determinant that confers such resistance is easy to transfer between *Brassica*, in particular *Brassica oleracea* varieties.

In the research leading to the present invention new *Brassica* plants, in particular *Brassica oleracea* plants were developed which show a resistance to clubroot. It was found that these new plants show an altered resistance pattern to clubroot.

The present invention thus provides a *Brassica* plant, in particular a *Brassica oleracea* plant carrying a genetic determinant that may comprise QTL1 and/or QTL2 and/or QTL3, which genetic determinant confers resistance to *Plasmodiophora brassicae*, and is as present in and obtainable from plants that are grown from seeds which were deposited with the NCIMB under NCIMB accession number 41851.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Seeds of *Brassica oleracea* var. italica Line 82 that comprise the genetic determinant of the invention which confers the resistance against *Plasmodiophora brassicae* as described herein were deposited with NCIMB Ltd, Ferguson Building, Craibstone 5 Estate, Bucksburn, Aberdeen AB21 9YA, UK on 27 Jun. 2011 under deposit accession number NCIMB 41851.

The Deposits with NCIMB Ltd, under deposit accession number NCIMB 41851 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

DETAILED DESCRIPTION OF THE INVENTION

Figure 1:
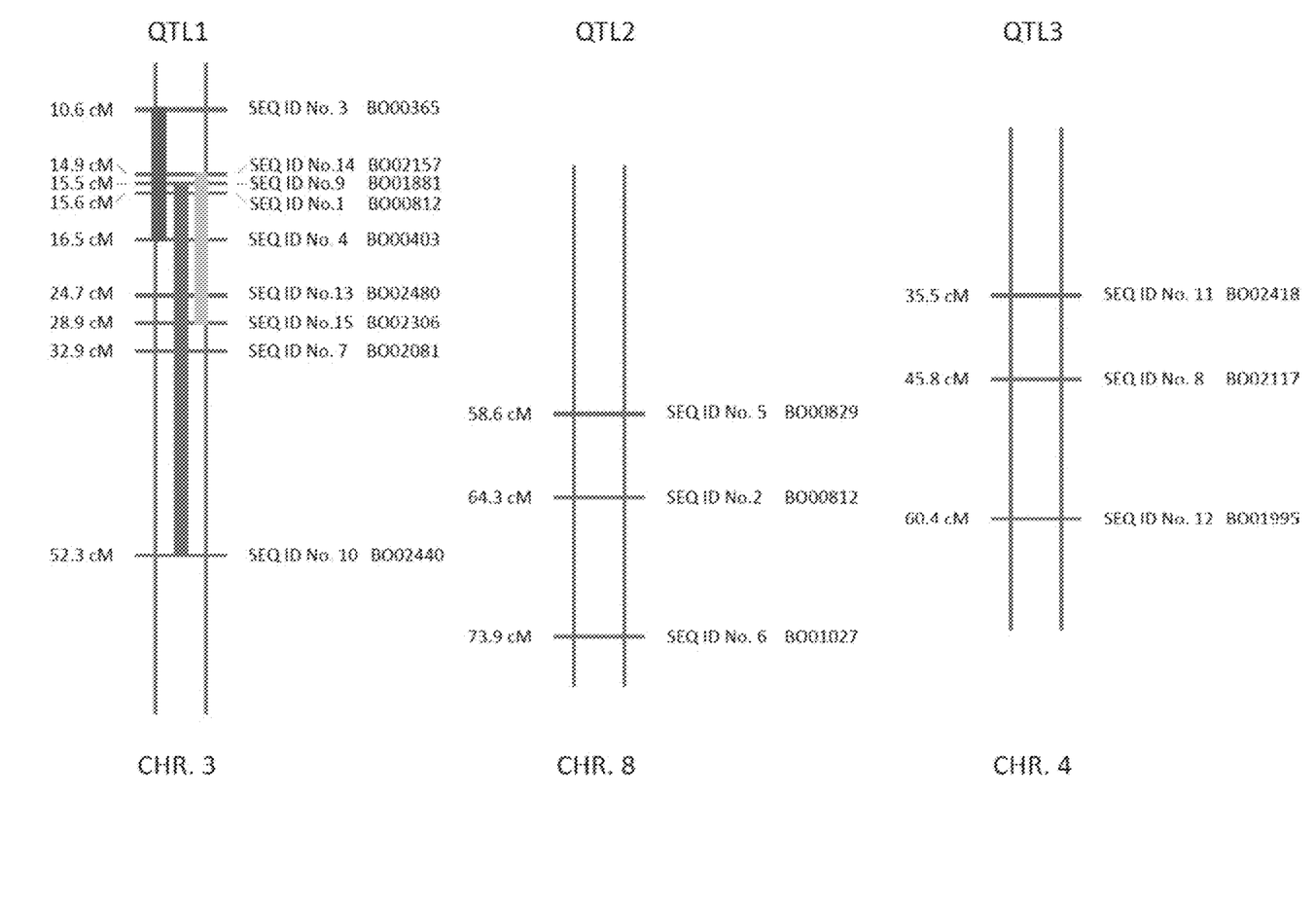
FIG. 1 schematically shows the location of the different QTLs on their chromosomes.

Research that led to the present invention furthermore showed that the genetic determinant of the invention that leads to resistance to *Plasmodiophora brassicae* has more than one QTL and that those QTLs are located on separate chromosomes of the *Brassica* genome, in particular the *Brassica oleracea* genome.

The present invention thus provides a *Brassica* plant, in particular a *Brassica oleracea* plant which may comprise a genetic determinant which confers resistance to *Plasmodio-*

*phora brassicae*, wherein said genetic determinant is characterised by the presence of at least:
- QTL1 or a *Plasmodiophora brassicae* resistance conferring part thereof, located on chromosome 3 and/or
- QTL2 or a *Plasmodiophora brassicae* resistance conferring part thereof, located on chromosome 8 and/or
- QTL3 or a *Plasmodiophora brassicae* resistance conferring part thereof, located on chromosome 4

In one embodiment the genetic determinant conferring resistance to *Plasmodiophora brassicae* is characterised by the presence of at least:
- QTL1 or a *Plasmodiophora brassicae* resistance conferring part thereof, or
- QTL2 or a *Plasmodiophora brassicae* resistance conferring part thereof, or
- QTL3 or a *Plasmodiophora brassicae* resistance conferring part thereof, or
- QTL1 or a *Plasmodiophora brassicae* resistance conferring part thereof, and QTL2 or a *Plasmodiophora brassicae* resistance conferring part thereof, or
- QTL1 or a *Plasmodiophora brassicae* resistance conferring part thereof, and QTL3 or a *Plasmodiophora brassicae* resistance conferring part thereof, or
- QTL1 or a *Plasmodiophora brassicae* resistance conferring part thereof, and QTL2 or a *Plasmodiophora brassicae* resistance conferring part thereof and QTL3 or a *Plasmodiophora brassicae* resistance conferring part thereof The combination of two, preferably three resistance-conferring QTLs leads to a higher level of resistance to *Plasmodiophora brassicae*, in particular to a set of *P. brassicae* isolates.

Furthermore, it was found during the research leading to the present invention that in one embodiment, QTL1 or a *Plasmodiophora brassicae* resistance conferring part thereof, is located on chromosome 3, between marker BO00365 (SEQ ID No. 3) and marker BO00403 (SEQ ID No. 4) and linked to marker BO00812 (SEQ ID No. 1).

Alternatively, QTL1 or a *Plasmodiophora brassicae* resistance conferring part thereof, is located on chromosome 3, between marker BO01881 (SEQ ID No.9) and marker BO02440 (SEQ ID No. 10) and linked to marker BO02081 (SEQ ID No. 7).

Alternatively, QTL1 or a *Plasmodiophora brassicae* resistance conferring part thereof, is located on chromosome 3, between marker BO02157 (SEQ ID No.14) and marker BO02306 (SEQ ID No.15)s and linked to marker BO02480 (SEQ ID No.13).

In a further embodiment of the present invention, QTL2 or a *Plasmodiophora brassicae* resistance conferring part thereof, is located on chromosome 8 and located between marker BO00829 (SEQ ID No. 5) and marker BO01007 (SEQ ID No. 6) and linked to marker BO01026 (SEQ ID No. 2).

In a further embodiment of the present invention, QTL3 or a *Plasmodiophora brassicae* resistance conferring part thereof, is located on chromosome 4 and located between marker BO02418 (SEQ ID No. 11) and marker BO01995 (SEQ ID No. 12) and linked to marker BO02117 (SEQ ID No. 8).

In one embodiment, a *Brassica* plant, in particular a *Brassica oleracea* plant of the invention may comprise a genetic determinant which confers resistance to *Plasmodiophora brassicae*, wherein said genetic determinant is characterised by the presence of at least:
- QTL1 or a *Plasmodiophora brassicae* resistance conferring part thereof, which in deposit NCIMB 41851 is linked to molecular marker characterized by SEQ ID No. 1, SEQ ID No. 3, and SEQ ID No. 4; and/or
- QTL2 or a *Plasmodiophora brassicae* resistance conferring part thereof, which in deposit NCIMB 41851 is linked to molecular marker characterized by SEQ ID No. 2, SEQ ID No. 5, and SEQ ID No. 6
- QTL3 or a *Plasmodiophora brassicae* resistance conferring part thereof, which in deposit NCIMB 41851 is linked to molecular marker characterized by SEQ ID No. 8, SEQ ID No. 11, and SEQ ID No. 12

Alternatively, QTL1 or a *Plasmodiophora brassicae* resistance conferring part thereof, is in deposit NCIMB 41851 linked to molecular markers characterized by SEQ ID No. 7, SEQ ID No. 9 and SEQ ID No. 10.

Alternatively, QTL1 or a *Plasmodiophora brassicae* resistance conferring part thereof, is in deposit NCIMB 41851 linked to molecular markers characterized by SEQ ID No. 13, SEQ ID No. 14 and SEQ ID No. 15.

The invention in particular relates to *Brassica* plants, in particular *Brassica oleracea* plants, carrying a genetic determinant that may comprise QTL1 and/or QTL2 and/or QTL3, which genetic determinant confers resistance to *Plasmodiophora brassicae*, in particular to the *Plasmodiophora brassicae* strain referred to as 16/3/30 according to the ECD differential set (Buczacki et al., Trans Br. Mycol. Soc. 65, 295-303, (1975)).

In a preferred embodiment, the invention in particular relates to *Brassica* plants, in particular *Brassica oleracea* plants, carrying a genetic determinant that may comprise QTL1 and QTL3, which genetic determinant confers resistance to *Plasmodiophora brassicae*, in particular to the *Plasmodiophora brassicae* strain referred to as 16/3/30 according to the ECD differential set (Buczacki et al., Trans Br. Mycol. Soc. 65, 295-303, (1975)).

In another embodiment, the invention relates to *Brassica* plants, in particular *Brassica oleracea* plants carrying a genetic determinant that may comprise QTL1 and/or QTL2 and/or QTL3, which genetic determinant confers resistance to *Plasmodiophora brassicae*, in particular to the *Plasmodiophora brassicae* strain referred to as 31/31/31 according to the ECD differential set (Buczacki et al., Trans Br. Mycol. Soc. 65, 295-303, (1975)).

In a preferred embodiment, the invention relates to *Brassica* plants, in particular *Brassica oleracea* plants carrying a genetic determinant that may comprise QTL1 and QTL2, which genetic determinant confers resistance to *Plasmodiophora brassicae*, in particular to the *Plasmodiophora brassicae* strain referred to as 31/31/31 according to the ECD differential set (Buczacki et al., Trans Br. Mycol. Soc. 65, 295-303, (1975)). In a further embodiment, the invention relates to *Brassica* plants, in particular *Brassica oleracea* plants carrying a genetic determinant that may comprise QTL1 and/or QTL2 and/or QTL3, which genetic determinant confers resistance to *Plasmodiophora brassicae*, in particular to the *Plasmodiophora brassicae* strains referred to as 16/2/30, 31/31/12 and 16/14/29 according to the ECD differential set (Buczacki et al., Trans Br. Mycol. Soc. 65, 295-303, (1975)).

In a preferred embodiment, the invention relates to *Brassica* plants, in particular *Brassica oleracea* plants carrying a genetic determinant that may comprise QTL1 and/or QTL2 and/or QTL3, which genetic determinant confers resistance to *Plasmodiophora brassicae*, in particular to the *Plasmodiophora brassicae* strains referred to as 16/3/30 and 31/31/31 according to the ECD differential set (Buczacki et al., Trans Br. Mycol. Soc. 65, 295-303, (1975)).

The present invention also relates to a *Brassica* plant, in particular a *Brassica oleracea* plant, which may comprise the genetic determinant heterozygously, and which genetic determinant is obtainable from plants grown from seeds of which a representative sample is deposited with the NCIMB under NCIMB accession number 41851.

In a further embodiment, the invention relates to a *Brassica* plant, in particular a *Brassica oleracea* plant which may comprise a genetic determinant that confers resistance to *Plasmodiophora brassicae*, wherein said genetic determinant is obtainable by introgression from a plant grown from seed that was deposited with the NCIMB, under accession number NCIMB 41851.

The invention further provides a *Brassica* plant, in particular a *Brassica oleracea* plant which may comprise a genetic determinant that confers resistance to *Plasmodiophora brassicae*, wherein said resistance is introgressed from a plant grown from seed that was deposited with the NCIMB, under accession number NCIMB 41851.

For the skilled breeder who wishes to introgress a trait into a plant it is sufficient to know the phenotype and to have a source of the trait and to optionally have markers to follow the trait in breeding. In the present invention, the skilled person has a source of the trait in the form of the deposit and knows what phenotype to look for, namely clubroot resistance. In addition, he can dispose of markers to more easily follow inheritance of the trait.

More in particular, it should be noted that if the selection criterion or criteria is or are clearly defined, the skilled person will be able to identify the descendants that carry the trait in any further generation. For the trait of the invention descendants from a cross between a plant not carrying the genetic determinant that confers resistance to *Plasmodiophora brassicae* and a plant carrying the genetic determinant that confers resistance to *Plasmodiophora brassicae* of which representative seeds were deposited under accession number NCIMB 41851 that carry that trait can be found by growing F2 plants from seeds that are the result from the initial cross and a selfing step, and selecting plants that are resistant to clubroot.

According to the invention a *Brassica* plant is provided, in particular a *Brassica oleracea* plant, which may comprise a genetic determinant that confers resistance to *Plasmodiophora brassicae*, which plant is obtainable by:
 a) growing plants from seeds of the deposit, deposited under accession number NCIMB 41851;
 b) growing plants in a *Plasmodiophora brassicae* infested environment;
 c) selecting plants showing resistance to *Plasmodiophora brassicae*, by not forming clubs;
 d) crossing a plant selected in step c with a plant not resistant to *Plasmodiophora brassicae* to obtain a F1 population;
 e) selfing plants from the F1 to obtain a F2 population; and
 f) repeating steps b) and c) to identify plants showing resistance to clubroot.

Alternatively, the selection step as described in step c) is performed by genotyping the plants by making use of the molecular SNP markers that are disclosed in this application. As a result, also the selection as repeated in step f) can be performed by making use of said molecular markers.

In the absence of molecular markers, or in the instance that recombination between the genetic determinant and the marker has taken place so that the marker is not predictive anymore, equivalence of genetic determinants can be determined by the well-known allelism test, more specifically designated as complementation test. To perform an allelism test, a tester plant which is homozygous for the known determinant of the invention is crossed with material to be tested that is also homozygous for its genetic determinant. When no segregation for the trait to be observed is present in the F2 of the cross, the genetic determinants have been proven to be equivalent or the same.

When more than one gene is responsible for a certain trait, and an allelism test is done to determine equivalence, the skilled person doing the test has to make sure that all relevant genes are present homozygously for the test to work properly.

The tester plant is suitably a plant of deposit NCIMB 41851, or a progeny plant of the deposit showing resistance to clubroot.

The *Brassica* plant of the invention is preferably a *Brassica oleracea* plant, but can also be any other plant of the genus *Brassica* into which the skilled person can introgress the genetic determinant of the invention, e.g. the following *Brassica* species: *Brassica oleracea*, *Brassica napus*, *Brassica campestris*, *Brassica cretica*, *Brassica rapa*, *Brassica juncea*, and *Brassica nigra*. The skilled person knows how to make interspecific crosses with these species, e.g. by means of embryo rescue, protoplast fusion, and other related technologies.

The invention relates to *Brassica oleracea* plants of the following varieties:
 var. acephala DC. (kales)
 var. botrytis L. (cauliflower, romanesco)
 var. capitata L. (red, white, savoy cabbage)
 var. gemmifera DC. (brussels sprouts)
 var. gongylodes L. (kohlrabi)
 var. italica Plenck. (broccoli, calabrese)
 var. sabauda L. (savoy cabbage)
 var. sabellica (collards)
 var. selensia (borecole)
 var. albiflora Sun [=*B. alboglabra*] (Chinese kale)
 var. alboglabra [=*B. alboglabra*] (Chinese kale)
 var. chinensis Prain (burma sarson)
 var. fimbriata Mill. (kitchen kale)
 var. fruticosa Metz. (thousand-head kale)
 var. tronchuda L. H. Bailey (tronchuda cabbage)
 var. costata (Portugese cabbage)
 var. medullosa (marrow stem kale)
 var. pamifolia (kale, Jersey kale)
 var. ramona (thousand-head kale)

Preferred are the varieties broccoli, cauliflower, romanesco, red cabbage, white cabbage, savoy cabbage and kohlrabi.

According to a further aspect thereof, the invention relates to seed of the *Brassica* plants, in particular *Brassica oleracea* plants, that comprise the genetic determinant causing resistance to *Plasmodiophora brassicae* as found in seed with deposit accession number NCIMB 41851.

The invention also relates to seed of the *Brassica* plant, in particular *Brassica oleracea* plant, of the invention that is capable of growing into a *Brassica oleracea* plant of the invention.

The invention furthermore, relates to hybrid seed and to a method of producing hybrid seeds which may comprise crossing a first parent plant with a second parent plant and harvesting the resultant hybrid seed. In case the trait is recessive, both parents need to be homozygous for the resistance trait in order for the hybrid seed to carry the trait of the invention. They need not necessarily be uniform for other traits. Both parents thus carry the genetic determinant causing the resistance to *Plasmodiophora brassicae* in homozygous form.

It is clear that a parent *Brassica* plant, in particular a parent *Brassica oleracea* plant that provides the genetic determinant of the invention is not necessarily a plant grown directly from the deposited seeds. The parent can also be a progeny plant from the seed or a progeny plant from seeds that are identified to have or to have acquired the genetic determinant causing the trait of the invention by other means.

The invention also relates to progeny of a *Brassica* plant, in particular *Brassica oleracea* plant, of the invention, which progeny is resistant to *Plasmodiophora brassicae*. Such progeny can be produced by sexual or vegetative reproduction of a plant of the invention or a progeny plant thereof. The progeny carries the genetic determinant that causes the trait of resistance to *Plasmodiophora brassicae* and that is as found in seed with deposit accession number NCIMB 41851, either in homozygous or heterozygous form.

When the genetic determinant of the invention is homozygously present, the progeny plant displays the resistance trait in the same or in a similar way as the plant grown from seed of which a representative sample was deposited under accession number NCIMB 41851. This means that such progeny has the same *Plasmodiophora brassicae* resistance characteristics as claimed for the *Brassica* plant, in particular *Brassica oleracea* plants of the invention. In addition to this, the plant may be modified in one or more other characteristics. Such additional modifications are for example effected by mutagenesis or by transformation with a transgene.

As used herein the word "progeny" is intended to mean the offspring or the first and all further descendants from a cross with a plant of the invention that shows the resistance trait and/or carries the genetic determinant underlying the trait. Progeny of the invention may comprise descendants of any cross with a plant of the invention that carries the genetic determinant causing the resistance trait. Such progeny is for example obtainable by crossing a first *Brassica* plant, in particular a *Brassica oleracea* plant with a second *Brassica* plant, in particular a *Brassica oleracea* plant, wherein one of the plants was grown from seeds of which a representative sample was deposited under NCIMB accession number 41851, but can also be the progeny of any other *Brassica* plant, in particular any other *Brassica oleracea* plant, carrying the genetic determinant as present in NCIMB 41851.

The said progeny plants comprise a genetic determinant that may comprise one or more QTLs causing the resistance of the invention, wherein the said genetic determinant is obtainable from a *Brassica* plant, in particular a *Brassica oleracea* plant grown from seeds of which a representative sample was deposited under NCIMB accession number 41851. The resistance trait thus has a genetic basis in the genome of a *Brassica oleracea* plant, and for example by using the bioassay described in Example 1 *Brassica oleracea* plants can be identified as being plants of the invention.

The invention further relates to parts of a *Brassica oleracea* plant of the invention, that are suitable for sexual and vegetative reproduction, i.e. propagation material, wherein said propagation material may comprise the genetic determinant causing resistance to *Plasmodiophora brassicae* of the invention. Such parts are for example selected from the group consisting of microspores, pollen, ovaries, ovules, embryo sacs and egg cells.

In addition, the invention relates to parts of the *Brassica oleracea* plant of the invention that are suitable for vegetative reproduction, in particular cuttings, roots, stems, cells, protoplasts, and tissue cultures of the *Brassica oleracea* plant of the invention. The tissue culture may comprise regenerable cells, Such a tissue culture can be derived from leaves, pollen, embryos, cotyledons, hypocotyls, meristematic cells, root tips, anthers, flowers, seeds and stems. The propagation material carries the genetic determinant that causes the resistance to *Plasmodiophora brassicae* of the invention, either in homozygous or heterozygous form.

The invention further relates to a *Brassica oleracea* plant grown or regenerated from the said propagation material of a plant of the invention, which *Brassica oleracea* plant is resistant to *Plasmodiophora brassicae*. The resistance phenotype is as found in plants grown from seeds having NCIMB accession number 41851 and the genetic determinant underlying the resistance is as present in the said seeds.

The invention further relates to a cell of a *Brassica oleracea* plant of the invention, which cell may comprise a genetic determinant which confers resistance to *Plasmodiophora brassicae*, wherein the said determinant is as present in a *Brassica oleracea* plant grown from seeds of which a representative sample was deposited with the NCIMB under NCIMB accession number 41851. The said cell thus may comprise the genetic information encoding said resistance, in particular genetic information which is substantially identical, preferably completely identical to the genetic information encoding the said resistance trait of the *Brassica oleracea* plant grown from seeds of which a representative sample was deposited under NCIMB accession number 41851, more in particular the genetic determinant described herein. Preferably, the cell of the invention is part of a plant or plant part, but the cell may also be in isolated form.

In one embodiment, the invention relates to *Brassica oleracea* plants that comprise the genetic determinant causing the trait of the invention and that have acquired said genetic determinant by introduction of the genetic information that is responsible for the trait from a suitable source, either by conventional breeding, or genetic modification, in particular by cisgenesis or transgenesis. Cisgenesis is genetic modification of plants with a natural gene, encoding an (agricultural) trait from the crop plant itself or from a sexually compatible donor plant. Transgenesis is genetic modification of a plant with a gene from a non-crossable species or with a synthetic gene.

In one embodiment, the source from which the genetic information is acquired, in particular the genetic determinant, is formed by plants grown from the deposited seeds, or by sexual or vegetative descendants thereof.

The invention also relates to harvested parts of *Brassica oleracea* plants of the invention or parts thereof, to food products which may comprise harvested parts of *Brassica oleracea* plants of the invention or parts thereof, either in natural or optionally in processed form.

The harvested part or food product can be or may comprise a cabbage head, a curd, a stem, a leaf, a root, a sprout, a seed, or any other part of a *Brassica* plant. The harvested part may also be used for the production of bio-fuel. The food product or harvested part, may have undergone one or more processing steps. Such a processing step might comprise but is not limited to any one of the following treatments or combinations thereof: cutting, washing, cooking, steaming, baking, frying, pasteurizing, freezing, grinding, extracting oil, pickling, or fermenting. The processed form that is obtained is also part of this invention.

Another aspect of this invention relates to a nucleic acid molecule which is causative of resistance to *Plasmodiophora brassicae*. The said DNA molecule may comprise a DNA sequence, in particular which may comprise QTL1, which is positioned on chromosome 3 between markers BO00365 (SEQ ID NO: 3) and BO00403 (SEQ ID NO: 4), more in particular linked to marker BO00812 (SEQ ID NO: 1), or a resistance conferring part thereof.

Alternatively, said DNA sequence is positioned on chromosome 3 between marker BO01881 (SEQ ID No.9) and marker BO02440 (SEQ ID No. 10), more in particular linked to marker BO02081 (SEQ ID No. 7).

Alternatively, said DNA sequence is positioned on chromosome 3 between marker BO02157 (SEQ ID No.14) and marker BO02306 (SEQ ID No.15), more in particular linked to marker BO02480(SEQ ID No.13).

In yet another aspect the invention relates to a nucleic acid molecule which is causative of resistance to *Plasmodiophora brassicae*. The said DNA molecule may comprise a DNA sequence, which in particular may comprise QTL2, which is positioned on chromosome 8 between markers BO00829 (SEQ ID NO: 5) and BO01007 (SEQ ID NO: 6), more in particular linked to marker BO01026 (SEQ ID NO: 2), or a resistance conferring part thereof.

In a further aspect, the invention relates to a nucleic acid molecule which is causative of resistance to *Plasmodiophora brassicae*. The said DNA molecule may comprise a DNA sequence, in particular which may comprise QTL3, which is positioned on chromosome 4 between markers BO02418 (SEQ ID No. 11) and BO01995 (SEQ ID No. 12), more in particular linked to marker BO02117 (SEQ ID No. 8), or a resistance conferring part thereof.

Linked to the marker is intended to mean that the chance that there is a recombination event between said marker and the QTL is lower than the chance that there is a recombination event between the QTL and any other markers. Preferably, it is intended to mean that said marker is genetically closest to said QTL.

The invention also relates to the use of the markers designated as SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 12, SEQ ID No. 13, SEQ ID No. 14 and SEQ ID No. 15 to identify or develop *Brassica oleracea* plants that are resistant to *Plasmodiophora brassicae*.

In a further embodiment, the invention also relates to the use of the markers designated as SEQ ID NO. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 12, SEQ ID No. 13, SEQ ID No. 14 and SEQ ID No. 15 to develop other markers linked to QTL1 and/or QTL2 and/or QTL3.

The invention also relates to the germplasm of plants of the invention. The germplasm is constituted by all inherited characteristics of an organism and according to the invention encompasses at least the resistance trait of the invention. The germplasm can be used in a breeding program for the development of *Brassica oleracea* plants that are resistant to *Plasmodiophora brassicae*.

The invention further relates to the use of a *Brassica oleracea* plant of the invention in breeding to confer resistance against *Plasmodiophora brassicae*.

In one aspect the invention relates to a method for the production of a *Brassica* plant, in particular a *Brassica oleracea* plant, which may comprise a genetic determinant that confers resistance to *Plasmodiophora brassicae* and is as found in seed with deposit accession number NCIMB 41851, which may comprise
  a) crossing a plant which may comprise the genetic determinant that leads to the trait with another plant;
  b) selfing the resulting F1 for obtaining F2 plants;
  c) selecting plants that have the trait in the F2;
  d) optionally performing one or more additional rounds of selfing or crossing, and subsequently selecting, for a plant which may comprise/showing the trait.

The word "trait" in the context of this application refers to the phenotype of the plant. The term "genetic determinant" is used for the genetic information in the genome of the plant that causes the trait. The genetic determinant thus may comprise QTL1 and/or QTL2 and/or QTL3. The term "QTL1 and/or QTL2 and/or QTL3" as used in this application may comprise in particular QTL1 or QTL2 or QTL3 or QTL1 and QTL2 or QTL1 and QTL3 or QTL2 and QTL3 or QTL1 and QTL2 and QTL3, more in particular QTL1 and QTL2 or QTL1 and QTL3. When a plant shows the trait of the invention, its genome may comprise the genetic determinant causing the trait of the invention, in particular the genetic determinant that is as found in seed with deposit accession number NCIMB 41851 and leads to clubroot resistance as defined herein. The plant thus has the genetic determinant of the invention. The genetic determinant is preferably present in homozygous state, but can also be present in heterozygous state. QTL1 and/or QTL2 and/or QTL3 are also preferably present in homozygous state, but can each separately or in any combination also be present in heterozygous state It is clear that the parent that provides the trait of the invention is not necessarily a plant grown directly from the deposited seeds. The parent can also be a progeny plant from the seed or a progeny plant from seeds that are identified to have the trait of the invention by other means.

In one aspect, the invention relates to a method for production of a *Brassica* plant, in particular a *Brassica oleracea* plant which may comprise a genetic determinant that confers resistance to *Plasmodiophora brassicae*, which may comprise
  a) crossing a plant which may comprise the genetic determinant that leads to the trait with another plant;
  b) optionally backcrossing the resulting F1 with the preferred parent;
  c) selecting for plants that have the trait in the F2;
  d) optionally performing one or more additional rounds of selfing or crossing, and subsequently selecting, for a plant which may comprise the trait.

The invention additionally provides a method of introducing another desired trait into a *Brassica* plant, in particular a *Brassica oleracea* plant which may comprise a genetic determinant that causes resistance to *Plasmodiophora brassicae*, which may comprise:
  a) crossing a *Brassica* plant, in particular a *Brassica oleracea* plant that may comprise a genetic determinant that causes resistance to *Plasmodiophora brassicae*, representative seed of which were deposited under deposit number NCIMB 41851, with a second *Brassica* plant, in particular a *Brassica oleracea* plant that may comprise a desired trait to produce F1 progeny;
  b) selecting an F1 progeny that may comprise the genetic determinant that causes resistance to *Plasmodiophora brassicae* and the desired trait, preferably by means of molecular markers;

c) selfing the F1 progeny and selecting an F2 progeny that may comprise the genetic determinant that causes resistance to *Plasmodiophora brassicae* and the desired trait;

d) crossing the selected F2 progeny with either parent, to produce backcross progeny;

e) selecting backcross progeny which may comprise the desired trait and a genetic determinant that causes resistance to *Plasmodiophora brassicae*; and f) optionally repeating steps c) and d) one or more times in succession to produce selected fourth or higher backcross progeny that may comprise the desired trait and a genetic determinant that causes resistance to *Plasmodiophora brassicae*. The invention includes a *Brassica* plant, in particular a *Brassica oleracea* plant produced by this method.

The selection step as described in step c) is suitably performed by genotyping the plants by making use of the molecular SNP markers that are disclosed in this application. As a result, also the selection steps as repeated in step f) can be performed by making use of said molecular markers.

Selection for plants which may comprise a genetic determinant that causes resistance to *Plasmodiophora brassicae* is for example done in the F1 by using marker BO00812 and marker BO01026 (SEQ ID No. 1 and SEQ ID No. 2, respectively). In another aspect selection for the trait of the invention is started in the F2 of a cross or alternatively of a backcross. Selection of plants in the F2 can be done phenotypically as well as by using the said marker(s) which directly or indirectly detect the genetic determinant underlying the trait.

In a further embodiment selection for plants which may comprise a genetic determinant that causes resistance to *Plasmodiophora brassicae* is started in the F3 or a later generation.

The plant which may comprise the genetic determinant is preferably a hybrid plant but can also be a plant of an inbred line, a doubled haploid, or of a segregating population.

The invention further provides a method for the production of a *Brassica* plant, in particular a *Brassica oleracea* plant, which may comprise the genetic determinant that causes resistance to *Plasmodiophora brassicae* of the invention by using a doubled haploid generation technique to generate a doubled haploid line which may comprise the said trait.

The invention furthermore relates to hybrid seed that can be grown into a plant which may comprise the genetic determinant that causes resistance to *Plasmodiophora brassicae* of the invention and to a method for producing such hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid *Brassica* plant, in particular a *Brassica oleracea* plant which may comprise the genetic determinant that causes resistance to *Plasmodiophora brassicae* of the invention, which may comprise crossing a first parent *Brassica* plant, in particular a *Brassica oleracea* parent plant with a second parent *Brassica* plant, in particular a *Brassica oleracea* parent plant and harvesting the resultant hybrid seed, wherein the first parent plant and/or the second parent plant may comprise the genetic determinant that causes resistance to *Plasmodiophora brassicae* of the invention, and growing said hybrid seeds into hybrid plants which may comprise a genetic determinant that causes resistance to *Plasmodiophora brassicae*.

The invention also relates to a method for the production of a *Brassica* plant, in particular a *Brassica oleracea* plant which may comprise the genetic determinant of the invention that causes resistance to *Plasmodiophora brassicae* by using a seed that may comprise the genetic determinant that causes resistance to *Plasmodiophora brassicae* for growing the said *Brassica* plant, in particular said *Brassica oleracea* plant. The seeds are suitably seeds of which a representative sample was deposited with the NCIMB under deposit number NCIMB 41851.

The invention also relates to a method for seed production which may comprise growing *Brassica* plants, in particular *Brassica oleracea* plants from seeds of which a representative sample was deposited with the NCIMB under deposit number NCIMB 41851, allowing the plants to produce seeds, and harvesting those seeds. Production of the seeds is suitably done by crossing or selfing.

In one embodiment, the invention relates to a method for the production of a *Brassica* plant, in particular a *Brassica oleracea* plant, which may comprise a genetic determinant that causes resistance to *Plasmodiophora brassicae* by using tissue culture.

The invention furthermore relates to a method for the production of a *Brassica* plant, in particular a *Brassica oleracea* plant, which may comprise the genetic determinant that causes resistance to *Plasmodiophora brassicae* of the invention by using vegetative reproduction.

In one embodiment, the invention relates to a method for the production of a *Brassica* plant, in particular a *Brassica oleracea* plant, which may comprise a genetic determinant that causes resistance to *Plasmodiophora brassicae* by using a method for genetic modification to introgress the said trait into the *Brassica* plant, in particular the *Brassica oleracea* plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of *Brassica* plants, in particular *Brassica oleracea* plants that comprise the genetic determinant that causes resistance to *Plasmodiophora brassicae* of the invention wherein germplasm which may comprise said trait is used. Representative seed of said plant which may comprise the genetic determinant and being representative for the germplasm has deposit number NCIMB 41851.

In a further embodiment the invention relates to a method for the production of a *Brassica* plant, in particular a *Brassica oleracea* plant which may comprise the genetic determinant that causes resistance to *Plasmodiophora brassicae* of the invention wherein progeny or propagation material of a plant which may comprise the genetic determinant conferring said trait is used as a source to introgress the said trait into another *Brassica* plant, in particular another *Brassica oleracea* plant. Representative seed of said plant which may comprise the genetic determinant was deposited under deposit number NCIMB 41851.

The invention provides preferably a *Brassica* plant, in particular a *Brassica oleracea* plant, which may comprise the genetic determinant that causes resistance to *Plasmodiophora brassicae* of the invention, which plant is obtainable by any of the methods herein described and/or familiar to the skilled person.

The invention relates to a cell of a *Brassica* plant, in particular a *Brassica oleracea* plant, which plant carries the genetic determinant that may comprise QTL1 and/or QTL2 and/or QTL3 as described herein, which confers resistance to *Plasmodiophora brassicae*, as present in a *Brassica* plant, in particular a *Brassica oleracea* plant grown from seed deposit accession number 41851.

The invention further relates to a cell of a *Brassica* plant, in particular a *Brassica oleracea* plant, which plant carries a genetic determinant that may comprise QTL1 and/or QTL2 and/or QTL3, which confers resistance to *Plasmodiophora brassicae*, as present in a *Brassica* plant, in particular a *Brassica oleracea* plant grown from seed as deposited with NCIMB on 27 Jun. 2011 and having the accession number 41851. Said *Brassica* plant, in particular a *Brassica oleracea* plant is obtainable by crossing a *Brassica* plant, in particular a *Brassica oleracea* plant with a second *Brassica* plant, in particular a *Brassica oleracea* plant grown from seed as deposited with NCIMB on 27 Jun. 2011 and having the accession number 41851, and selecting for a *Brassica* plant, in particular a *Brassica oleracea* plant that shows a resistance to the pathogen in a disease test, preferably a marker test as present in the *Brassica* plant, in particular the *Brassica oleracea* plant of the invention which carries a genetic determinant that may comprise QTL1 and/or QTL2 and/or QTL3, which confers resistance to *Plasmodiophora brassicae*.

In one embodiment, the invention relates to the use of seeds with NCIMB accession number 41851, for transferring the genetic determinant that may comprise QTL1 and/or QTL2, which confers resistance to *Plasmodiophora brassicae*, into another *Brassica* plant, in particular a *Brassica oleracea* plant.

In another embodiment, the invention relates to the use of a *Brassica* plant, in particular a *Brassica oleracea* plant, which plant carries a genetic determinant that may comprise QTL1 and/or QTL2 and/or QTL3, which confers resistance to *Plasmodiophora brassicae*, as present in and obtainable from a *Brassica* plant, in particular a *Brassica oleracea* plant, grown from seed with NCIMB number 41851, as a crop.

The invention also relates to the use of a *Brassica* plant, in particular a *Brassica oleracea* plant, which carries a genetic determinant that may comprise QTL1 and/or QTL2 and/or QTL3, which confers resistance to *Plasmodiophora brassicae*, as present in a *Brassica* plant, in particular a *Brassica oleracea* plant grown from seed with accession number 41851, as a source of seed.

In yet another embodiment, the invention relates to the use of a *Brassica* plant, in particular a *Brassica oleracea* plant, which carries a genetic determinant that may comprise QTL1 and/or QTL2 and/or QTL3, which confers resistance to *Plasmodiophora brassicae*, as present in a *Brassica* plant, in particular a *Brassica oleracea* plant grown from seed with NCIMB accession number 41851, as a source of propagating material.

Further, the invention relates to the use of a *Brassica* plant, in particular a *Brassica oleracea* plant, which carries a genetic determinant that may comprise QTL1 and/or QTL2 and/or QTL3, which confers resistance to *Plasmodiophora brassicae*, as present in a *Brassica* plant, in particular a *Brassica oleracea* plant grown from seed with NCIMB accession number 41851, for consumption.

In another embodiment, the invention relates to the use of a *Brassica* plant, in particular a *Brassica oleracea* plant, which carries a genetic determinant that may comprise QTL1 and/or QTL2, which confers resistance to *Plasmodiophora brassicae*, alleles as present in seeds with NCIMB accession number 41851, for conferring carries a genetic determinant that comprises QTL1 and/or QTL2 and/or QTL3, which confers resistance to *Plasmodiophora brassicae*, on a *Brassica* plant, in particular a *Brassica oleracea* plant.

In yet another embodiment, the invention relates to the use of a *Brassica* plant, in particular a *Brassica oleracea* plant, as a recipient of resistance alleles as present in seeds with NCIMB accession number 41851.

"Introgression" as used in this application is intended to mean introduction of a trait into a plant not carrying the trait by means of crossing and selection.

"Progeny" as used in this application is intended to mean the first and all further descendants from a cross with a plant of the invention that shows resistance to clubroot. Progeny of the invention are descendants of any cross with a plant of the invention that carries the trait that leads to resistance to clubroot.

"Progeny" also encompasses plants that carry the trait of the invention and are obtained from other plants of the invention by vegetative propagation or multiplication. Progeny is not only the first, but also all further generations as long as resistance to clubroot is retained. Progeny typically has an ancestor that is a plant having the ability to show resistance to clubroot, when grown in a field under clubroot infested conditions, or in a greenhouse inoculation test as described herein, as is found in plants grown from seed as deposited. An ancestor is intended to encompass not only the generation immediately prior to the plant but also multiple generations before that. More in particular, the ancestor is a plant from the deposited seed or a further generation descendent therefrom.

The term "genetic determinant" as used herein encompasses one or more QTLs, genes, or alleles. These terms are used interchangeably. A genetic determinant can be identified by the use of a molecular marker. A genetic determinant can alternatively be identified by the position on a genetic map, or by indication of the location on a linkage group or chromosome. When a genetic determinant is not linked to a specific molecular marker any longer, but its position on a chromosome as defined on a genetic map is unaltered, this genetic determinant is still the same as when it was linked to the molecular marker. The genetic trait that it confers is therefore also still the same. The "genetic trait" is the trait or characteristic that is conferred by the genetic determinant. The genetic trait can be identified phenotypically, for example by performing a bio-assay. However, also plant stages for which no phenotypic assay can be performed do carry the genetic information that leads to the genetic trait. "Trait" or "phenotypic trait" can be used instead of "genetic trait".

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

QTL Mapping and Marker Development

A large population consisting of 172 F2 *Brassica oleracea* plants was used for mapping the resistance to *Plasmodio-*

*phora brassicae*. These F2 plants were the result of a first cross between Line 82 and the clubroot susceptible broccoli plant EA2479 (Rijk Zwaan), and a subsequent selfing cross. The population was inoculated with a clubroot isolate having the ECD code 16/3/30 and according the protocol as described in Example 3. In total 163 SNP markers were analysed, of which 154 markers were found to be polymorphic.

Remarkably, 2 QTLs were identified that contribute to the resistance, both positioned on different chromosomes. The molecular SNP markers that correlated most closely to the QTLs are presented in Table 1.

SEQ ID No. 1 may comprise the presence of a SNP from nucleotide C (wild type) to A at chromosome 3. The position can also be indicated as the $42^{nd}$ position (bold) in the nucleotide sequence shown in Table 1.

SEQ ID No. 2 may comprise the presence of a SNP from nucleotide G (wild type) to C at chromosome 8. The position can also be indicated as the $40^{th}$ position (bold) in the nucleotide sequence shown in Table 1.

SEQ ID No. 3 may comprise the presence of a SNP from nucleotide C (wild type) to G at chromosome 3. The position can also be indicated as the $42^{nd}$ position (bold) in the nucleotide sequence shown in Table 1.

SEQ ID No. 4 may comprise the presence of a SNP from nucleotide T (wild type) to C at chromosome 3. The position can also be indicated as the $41^{st}$ position (bold) in the nucleotide sequence shown in Table 1.

SEQ ID No. 5 may comprise the presence of a SNP from nucleotide C (wild type) to A at chromosome 8. The position can also be indicated as the $43^{rd}$ position (bold) in the nucleotide sequence shown in Table 1.

SEQ ID No. 6 may comprise the presence of a SNP from nucleotide A (wild type) to G at chromosome 8. The position can also be indicated as the $40^{th}$ position (bold) in the nucleotide sequence shown in Table 1.

A first QTL which explained 18.5% of the variation was located on chromosome 3, having a LOD score of 10.24. The position of the QTL was determined to be between the markers designated as SEQ ID No 3. and SEQ ID No 4, the sequence of which is found in Table 1. In the F2 population and subsequent progeny this QTL was linked most closely to a SNP marker designated SEQ ID No.1, the sequence of which is found in Table 1. The borders of the preferred QTL region can be determined by the presence of SEQ ID No. 3 and SEQ ID No. 4.

A second QTL which explained 17.0% of the variation was located on chromosome 8, having a LOD score of 9.51. The position of the QTL was determined to be between the markers designated as SEQ ID No. 5 and SEQ ID No. 6, the sequence of which is found in Table 1. In the F2 population and subsequent progeny this QTL was linked most closely to a SNP marker designated as SEQ ID No. 2, the sequence of which is found in Table 1. The borders of the preferred QTL region can be determined by the presence of SEQ ID No. 5 and SEQ ID No. 6.

TABLE 1

Molecular SNP markers based on the population-specific genetic map, that in deposit numbers NCIMB 41815 are linked to QTL1 and QTL2, which confer resistance to *Plasmodiophora brassicae* in *Brassica* plants, in particular *Brassica oleracea* plants.

| Designation | Sequence | Related QTL |
| --- | --- | --- |
| SEQ ID No. 1<br>B000812 | ACAGAGTCTTCAAACATTTCATAGCACGAAGCTGA<br>GTTGCTAGTGTGGTTTCAGGTGCTGCTACTAACATT<br>GTTGGGATG | QTL1 |
| SEQ ID No. 2<br>B001026 | GTTAGTCTCATAGTTTACATACATACTCTGCTGGTA<br>ATACTCATGGGACGTTGGTGCTGAGTCCATCACGA<br>CCGTGTTG | QTL2 |
| SEQ ID No. 3<br>B000365 | TCAGATTCTCTGAAGTCAATCTTGTGTTCAACACCA<br>GCTTTGTTTATAATTGGCAATCCTACCTCTTCGTAT<br>GAGCCTCT | QTL1 |
| SEQ ID No. 4<br>B000403 | ATCATCTTCCATAGCTTTCACATGCTTTGTGGCTCC<br>CACGCTCACTCCAGTTCTGAGAACTTGCGTAACCA<br>ACTTCTCG | QTL1 |
| SEQ ID No. 5<br>B000829 | CTGCTTCCCTTTCCCAAACAAACCTCCAAACCAAGA<br>YCCCGAACCTGCCTCCGAAGCAGATGAAGTCTCCG<br>GCACAGGC | QTL2 |
| SEQ ID No. 6<br>B001007 | AATGAGCGAGGACGTGAGCGGGAACAAGTTCTTCG<br>ACGAGGCAATGATGGTGGAGCTAGCGCAGCAGAC<br>GGGTGATCTG | QTL2 |

The SNP sequences are linked to the respective QTLs in NCIMB 41851. The SNP sequences can be used as molecular markers for resistance to *Plasmodiophora brassicae* in *Brassica oleracea* plants of said deposit.

Example 2

Further QTL Mapping and Marker Development
(1)

A large population consisting of 182 F2 *Brassica oleracea* plants was used for mapping the resistance to *Plasmodiophora brassicae*. These F2 plants were the result of a first cross between Line 82 and the clubroot susceptible cauliflower plant LI5606 (Rijk Zwaan), and a subsequent selfing cross. The population was inoculated with a clubroot isolate having the ECD code 31/31/31 and according the protocol as described in Example 3. In total 785 SNP markers were analysed, of which 650 markers were found to be polymorphic.

Remarkably, 2 QTLs were identified that contribute to the resistance, positioned on chromosome 3 and chromosome 4. The QTL on chromosome 3 was found in the same region as QTL1 as described in Example 1. The molecular SNP markers that correlated most closely to the QTLs are presented in Table 2.

SEQ ID No. 7 may comprise the presence of a SNP from nucleotide G (wild type) to A at chromosome 3. The position can also be indicated as the $46^{th}$ position (bold) in the nucleotide sequence shown in Table 2.

SEQ ID No. 8 may comprise the presence of a SNP from nucleotide A (wild type) to T at chromosome 4. The position can also be indicated as the $42^{nd}$ position (bold) in the nucleotide sequence shown in Table 2.

SEQ ID No. 9 may comprise the presence of a SNP from nucleotide A (wild type) to G at chromosome 3. The position can also be indicated as the $40^{th}$ position (bold) in the nucleotide sequence shown in Table 2.

SEQ ID No. 10 may comprise the presence of a SNP from nucleotide C (wild type) to T at chromosome 3. The position can also be indicated as the $42^{nd}$ position (bold) in the nucleotide sequence shown in Table 2.

SEQ ID No. 11 may comprise the presence of a SNP from nucleotide T (wild type) to A at chromosome 4. The position can also be indicated as the $41^{st}$ position (bold) in the nucleotide sequence shown in Table 2.

SEQ ID No. 12 may comprise the presence of a SNP from nucleotide T (wild type) to G at chromosome 4. The position can also be indicated as the $43^{rd}$ position (bold) in the nucleotide sequence shown in Table 2.

A first QTL which explained 10.7% of the variation was located on chromosome 3, having a LPD score (the Bayesian equivalent of the LOD score) of 11.2. The position of the QTL was determined to be between the markers designated as SEQ ID No. 9 and SEQ ID No. 10, the sequence of which is found in Table 2. In the F2 population and subsequent progeny this QTL was linked most closely to a SNP marker designated SEQ ID No.7, the sequence of which is found in Table 2. The borders of the preferred QTL region can be determined by the presence of SEQ ID No. 9 and SEQ ID No. 10.

A second QTL which explained 7.2% of the variation was located on chromosome 4, having a LPD score of 5.4. The position of the QTL was determined to be between the markers designated as SEQ ID No. 11 and SEQ ID No. 12, the sequence of which is found in Table 2. In the F2 population and subsequent progeny this QTL was linked most closely to a SNP marker designated as SEQ ID No. 8, the sequence of which is found in Table 2. The borders of the preferred QTL region can be determined by the presence of SEQ ID No. 11 and SEQ ID No. 12.

Further QTL Mapping and Marker Development (2)

A large population consisting of 128 F2 *Brassica oleracea* plants was used for mapping the resistance to *Plasmodiophora brassicae*. These F2 plants were the result of a first cross between Line 82 and the clubroot susceptible broccoli plant EA2749 (Rijk Zwaan), and a subsequent selfing cross. The population was inoculated with a clubroot isolate having the ECD code 31/31/31 and according the protocol as described in Example 3. In total 785 SNP markers were analysed, of which 564 markers were found to be polymorphic.

Remarkably, a QTL was identified that contributes to the resistance, positioned on chromosome 3. The QTL on chromosome 3 was found in the same region as QTL1 as described in Example 1 and above in Example 2. The molecular SNP markers that correlated most closely to the QTL are presented in Table 2.

SEQ ID No. 13 may comprise the presence of a SNP from nucleotide G (wild type) to A at chromosome 3. The position can also be indicated as the $4^{th}$ position (bold) in the nucleotide sequence shown in Table 2.

SEQ ID No. 14 may comprise the presence of a SNP from nucleotide A (wild type) to T at chromosome 3. The position can also be indicated as the $43^{rd}$ position (bold) in the nucleotide sequence shown in Table 2.

SEQ ID No. 15 may comprise the presence of a SNP from nucleotide T (wild type) to C at chromosome 4. The position can also be indicated as the $45^{th}$ position (bold) in the nucleotide sequence shown in Table 2.

The QTL, which explained 25.4% of the variation, was located on chromosome 3, having a LPD score of 23.02. The position of the QTL was determined to be between the markers designated as SEQ ID No. 14 and SEQ ID No. 15, the sequence of which is found in Table 2. In the F2 population and subsequent progeny this QTL was linked most closely to a SNP marker designated SEQ ID No. 13, the sequence of which is found in Table 2. The borders of the preferred QTL region can be determined by the presence of SEQ ID No. 14 and SEQ ID No. 15.

TABLE 2

Molecular SNP markers based on the population-specific genetic map, that in deposit numbers NCIMB 41815 are linked to QTL1 and QTL3, which confer resistance to *Plasmodiophora brassicae* in *Brassica* plants, in particular *Brassica oleracea* plants.

| Designation | Sequence | Related QTL |
|---|---|---|
| SEQ ID No. 7<br>BO02081 | GGACTAGATTGGAATAGTAACCTAAATGAAGCAA<br>TGGAGGATGATAAAGAAGAAGTTGTTGGGGCTGC<br>GCAGGTCGAGA | QTL1 |
| SEQ ID No. 8<br>BO02117 | GATWGGGTCATCCGAATCCACACATCCTWCAGCA<br>CCTATCTTCTACTAAGTCTATCGTCATAAATAAGA<br>GATCCARAGG | QTL3 |
| SEQ ID No. 9<br>BO01881 | AGAGGTCCGTGGAATCCCATCTTACTGGATCGAC<br>AGTGAGCAACGGATAGGACCTGGGAACAAAATA<br>GCCTATAAGCTCC | QTL1 |

TABLE 2-continued

Molecular SNP markers based on the population-specific genetic map, that in deposit numbers NCIMB 41815 are linked to QTL1 and QTL3, which confer resistance to *Plasmodiophora brassicae* in *Brassica* plants, in particular *Brassica oleracea* plants.

| Designation | Sequence | Related QTL |
|---|---|---|
| SEQ ID No. 10 B002440 | GATGTCGGTGTAGAGACCTGGACCTTTCACCATTT TTGCTTTGCTTTGCTTMCTACCAMAAAGAACAAA AGATACCTCGA | QTL1 |
| SEQ ID No. 11 B002418 | AGCTTGGAGCTAGAGCGGAGGAGATGCGCAGGA AGCTAGTAGGATCAGTGACAGAAGGCAGCTCTTT TGCTGATTTAGA | QTL3 |
| SEQ ID No. 12 B001995 | CCACTGATGAGCGAAGGCATAAGCYARGGCTCTT TCCCGCTTGATCGTTGCTTCTTCCCTTTGATGTATC CTCCCYAAG | QTL3 |
| SEQ ID No. 13 B002480 | GGACACTTAAAAAAACCCCTTGCTCTCTTCAATAG CGTTATAAAGCAAATCAGCTTTCCTCTGATTCTTC CTCTCCACTT | QTL1 |
| SEQ ID No. 14 B002157 | GGAGAAATGAAGCGGAAAGTAAAAACACACACA CAGATTGAGTTTTTTTTCGTTTTACTTTTTCTGTT TTTTTTTTCT | QTL1 |
| SEQ ID No. 15 B002306 | CTCGGCTCTTTTGTTGGAGAGATACGAAGGTGGC GGAGATCTACCAGCGGCGGGATGAGGAGGGGTC GCCGGATTGCTCT | QTL1 |

Example 3

Identification of *Brassica oleracea* Plants Which Have Obtained the Resistance to Clubroot In this example, inoculation tests are described. The general protocol is provided, together with the results of experiments using plants of the invention and commercially available varieties.

In Table 3, an overview of infection symptoms and classification stadia of *Plasmodiophora brassicae* infected *Brassica* plants is given. Such an overview is used by phenotypically identifying clubroot resistant plants. In addition, it submitted that scores 2 and 3 sometimes taken together, representing an intermediate infection phenotype.

TABLE 3

Overview of infection symptoms and classification stadia of *Plasmodiophora brassicae* infected *Brassica* plants

| Score | Symptoms | Classification |
|---|---|---|
| 0 | No symptoms, clean roots | Highly resistant |
| 1 | Small clubs, only present on lateral roots | Intermediate resistant |
| 2 | Moderately sized clubs, also present on main root | Intermediate susceptible |
| 3 | Complete root system is heavily infested with large clubs | Highly susceptible |

In order to test whether plants are resistant to clubroot or not, about 20 seeds per line are sown in peat soil with a height of 8 cm. with approximately 2 cm of sowing soil on top. Two to seven days after sowing, the plants are inoculated with 2 ml of the inoculant containing spores of the *Plasmodiophora brassicae* isolates of interest. This can be a mixture of isolates or a single isolate. In this example, disease tests with an inoculant containing a single *Plasmodiophora brassicae* isolate. After inoculation, the plants are not watered for 2 to 3 days to prevent the spores to be flushed away. Successively, the inoculated plants are grown for 5 to 6 weeks under Dutch greenhouse conditions at a temperature of 23 to 25° C.

Example 4

During a clubroot disease test known susceptible and resistant varieties were sown to test whether the general conditions for a successful and reliable disease test were met. For the identification of clubroot isolates the ECD (European Clubroot Differential) set is used. This set consists out of 5 cultivars, selected out of each of the three *Brassica* species *B. rapa, B. napus* and *B. oleracea*. So, in total 15 cultivars were taken into account. These are referred to in Table 4 with the numbers 1 to 15 in the column "Differential numbers". If in a disease test, such a cultivar is found susceptible for a tested isolate, the corresponding denary number is added up with the denary numbers of other susceptible cultivars of this specific *Brassica* species. In this way, three numbers for the three *Brassica* species can be calculated.

In Table 4 the results of a disease test are given. In this test a specific isolate designated PLA-DE1145, was tested on the ECD set, on plants of the invention (t1) and on plants of the variety "Janin" (t2). In the column designated "PLA-DE1145" the results are listed in the following order of scores: 0, 1-2, 3. So, in this experiment the scores 1 and 2 are taken together in one group. The differential test showed that the variety "Janin" is susceptible for the isolate designated PLA-DE1145, which is assigned the code 31/31/31 according to the ECD set. Plants of the invention were shown to be resistant.

TABLE 4

| Differential number | *Brassica* | Accession | Denary number | PLA-DE1145 | Code |
|---|---|---|---|---|---|
| 1 | *rapa* var. *pekinensis* | aaBBCC | 1 | 2-0-12 | 31 |
| 2 | *rapa* var. *pekinensis* | AabbCC | 2 | 2-0-11 | |
| 3 | *rapa* var. *pekinensis* | AABBcc | 4 | 2-4-5 | |

TABLE 4-continued

| Differential number | Brassica | Accession | Denary number | PLA-DE1145 Code | |
|---|---|---|---|---|---|
| 4 | rapa var. pekinensis | AABBCC | 8 | 2-1-10 | |
| 5 | rapa var. pekinensis | Granaat | 16 | 0-0-15 | |
| 6 | napus | Nevin | 1 | 0-0-14 | 31 |
| 7 | napus | Giant Rape | 2 | 0-0-13 | |
| 8 | napus | Line Dc126 | 4 | 0-0-15 | |
| 9 | napus | Clubroot Resistant | 8 | 0-0-13 | |
| 10 | napus | Wilhelmsburger | 16 | 0-0-15 | |
| 11 | oleracea var. capitata | Badger Shipper | 1 | 0-0-13 | 31 |
| 12 | oleracea var. capitata | Sachsener | 2 | 0-4-8 | |
| 13 | oleracea var. capitata | Jersey Queen | 4 | 0-0-15 | |
| 14 | oleracea var. capitata | Septa | 8 | 0-0-13 | |
| 15 | oleracea var. fimbriata | Verheul | 16 | 0-0-10 | |
| t1 | | Line 82 | | 10-1-2 | |
| t2 | | Janin | | 0-0-15 | |

Overview of the results of a clubroot differential test using the Plasmodiophora brassicae isolate PLA-DE1145

In Table 5, the results of an inoculation experiment with Plasmodiophora brassicae strain 31/31/31 are given. In this test the commercially available strains "Clarify" and "Clapton" are tested with the clubroot isolate that was designated 31/31/31 according the ECD test mentioned in Table 4. From Table 5, it follows that "Clapton" and "Clarify" can be considered to be susceptible for this clubroot isolate.

TABLE 5

Results from an inoculation experiment with Plasmodiophora brassicae strain 31/31/31

| Variety | Plot | Result |
|---|---|---|
| Clarify | 86 | 4/0/0/25 |
| Clarify | 150 | 0/0/0/28 |
| Clarify | 253 | 0/0/2/27 |
| Clarify | 11 | 0/7/0/17 |
| Clarify | 165 | 0/0/8/16 |
| Clapton | 71 | 2/0/0/20 |
| Clapton | 92 | 0/0/0/22 |
| Clapton | 12 | 1/5/0/18 |
| Clapton | 166 | 1/2/5/18 |

The invention is further described by the following numbered paragraphs:

1. A Brassica plant, in particular a Brassica oleracea plant carrying a genetic determinant that comprises QTL1 and/or QTL2 and/or QTL3, which confer resistance against Plasmodiophora brassicae, and which genetic determinant is present in plants that are grown from seeds which were deposited with the NCIMB under NCIMB accession number 41851.

2. The Brassica plant of paragraph 1 which comprises QTL1 and optionally QTL2 and/or QTL3, all preferably in homozygous state, and is resistant to Plasmodiophora brassicae.

3. The Brassica plant of paragraph 1 or 2, wherein the said genetic determinant as present in plants that are grown from the seeds of NCIMB deposit 41851 comprises:

QTL1, located on chromosome 3 between marker BO00365 (SEQ ID No. 3) and marker BO00403 (SEQ ID No. 4) and linked to marker BO00812 (SEQ ID NO. 1) or a Plasmodiophora brassicae resistant part thereof or;

QTL1, located on chromosome 3, between marker BO01881 (SEQ ID No.9) and marker BO02440 (SEQ ID No. 10) and linked to marker BO02081 (SEQ ID No. 7) or QTL1, located on chromosome 3, between marker BO02157 (SEQ ID No.14) and marker BO02306 (SEQ ID No.15)s and linked to marker BO02480 (SEQ ID No.13) and/or QTL2, located on chromosome 8 between marker BO00829 (SEQ ID No. 5) and marker BO1007 (SEQ ID No. 6), and linked to marker BO01026 (SEQ ID No. 2) or a Plasmodiophora brassicae resistant part thereof and/or;

QTL3, located on chromosome 4 between marker BO02418 (SEQ ID No. 11) and BO01995, (SEQ ID No. 12) and linked to marker BO02117 (SEQ ID No. 8)

4. Seed comprising the genetic determinant as defined in any one of the paragraphs 1-3.

5. Seed of paragraph 4, wherein the plant that can be grown from the seed is resistant to Plasmodiophora brassicae.

6. Progeny plant of a Brassica plant of any one of the paragraphs 1-3, or progeny of plants grown from seeds of paragraph 4 or paragraph 5, wherein the plant comprises the genetic determinant as defined in any one of the paragraphs 1-3.

7. Progeny plant of paragraph 6, wherein the progeny plant is resistant to Plasmodiophora brassicae.

8. Propagation material derived from a plant of any one of the paragraphs 1-3, wherein the propagation material comprises the genetic determinant as defined in any one of the paragraphs 1-3.

9. Propagation material capable of growing into a plant of anyone of the paragraphs 1-3.

10. Propagation material of paragraph 8 or 9, wherein the propagation material is selected from a group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts and cells.

11. Tissue culture of propagation material of anyone of the paragraphs 8-10.

12. Harvested part of a Brassica plant of any one of the paragraph 1-3, 6 or 7 which is in particular selected from the group consisting of cabbage head, curd, stem, leaf, sprout, seed, optionally in processed form.

13. Harvested part of paragraph 12, wherein the harvest part is a food product.

14. A nucleic acid molecule causative of resistance against Plasmodiophora brassicae, comprising a DNA sequence, which is linked to marker BO00812 (SEQ ID No. 1) located on chromosome 3, in particular located on chromosome 3 between marker BO00365 (SEQ ID No. 3) and marker BO00403 (SEQ ID No. 4), or a resistance conferring part of said nucleic acid molecule.

15. A nucleic acid molecule causative of resistance against Plasmodiophora brassicae, comprising a DNA sequence, which is linked to marker BO01026 (SEQ ID No. 2) located on chromosome 8, in particular located on chromosome 8 between marker BO00829 (SEQ ID No. 5) and marker BO01007 (SEQ ID No. 6), or a resistance conferring part of said nucleic acid molecule.

16. A nucleic acid molecule causative of resistance against Plasmodiophora brassicae, comprising a DNA sequence, which is linked to marker BO02117 (SEQ ID No. 8) located on chromosome 4, in particular located on chromosome 4 between marker BO02418 (SEQ ID No. 11) and marker BO01995 (SEQ ID No. 12), or a resistance conferring part of said nucleic acid molecule.

17. Use of the markers as defined in paragraph 3 and/or use of the nucleic acid molecules of paragraph 14 and/or 15 and/or 16, to identify or develop *Plasmodiophora brassicae* resistant plants, or develop other markers linked to the genetic determinant as defined in anyone of the paragraphs 1 to 3.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Brassica oleracea* plant comprising a genetic determinant, which confers resistance against *Plasmodiophora brassicae*,
   wherein the genetic determinant is present in plants that are grown from seeds which were deposited with the NCIMB under NCIMB accession number 41851, and
   wherein the genetic determinant comprises QTL1 and QTL3,
   wherein QTL1 is located on chromosome 3 between marker BO00365 (SEQ ID No: 3) and marker BO00403 (SEQ ID No: 4) and is linked to marker BO00812 (SEQ ID NO: 1), or is located on chromosome 3 between marker BO01881 (SEQ ID No: 9) and marker BO02440 (SEQ ID No: 10) and is linked to marker BO02081 (SEQ ID No: 7), or is located on chromosome 3 between marker BO02157 (SEQ ID No: 14) and marker BO02306 (SEQ ID No: 15) and is linked to marker BO02480 (SEQ ID No: 13), and
   wherein QTL3 is located on chromosome 4 between marker BO02418 (SEQ ID No: 11) and BO01995 (SEQ ID No: 12) and is linked to marker BO02117 (SEQ ID No: 8).

2. The *Brassica oleracea* plant as claimed in claim 1, which is resistant to *Plasmodiophora brassicae*.

3. The *Brassica oleracea* plant as claimed in claim 1, wherein QTL1 and QTL3 are in a homozygous state.

4. A *Brassica oleracea* seed comprising the genetic determinant as defined in claim 1.

5. The seed as claimed in claim 4, wherein the plant that can be grown from the seed is resistant to *Plasmodiophora brassicae*.

6. A progeny plant of a *Brassica oleracea* plant as claimed in claim 1, wherein the progeny plant comprises the genetic determinant as defined in claim 1.

7. The progeny plant as claimed in claim 6, wherein the progeny plant is resistant to *Plasmodiophora brassicae*.

8. A progeny plant of a *Brassica oleracea* plant grown from the seed of claim 4,
   wherein the progeny plant comprises a genetic determinant which confers resistance against *Plasmodiophora brassicae*,
   wherein the genetic determinant is present in plants that are grown from seeds which were deposited with the NCIMB under NCIMB accession number 41851,
   wherein the genetic determinant comprises QTL1 and QTL3,
   wherein QTL1 is located on chromosome 3 between marker BO00365 (SEQ ID No: 3) and marker BO00403 (SEQ ID No: 4) and is linked to marker BO00812 (SEQ ID NO: 1), or is located on chromosome 3 between marker BO01881 (SEQ ID No: 9) and marker BO02440 (SEQ ID No: 10) and is linked to marker BO02081 (SEQ ID No: 7), or is located on chromosome 3 between marker BO02157 (SEQ ID No: 14) and marker BO02306 (SEQ ID No: 15) and is linked to marker BO02480 (SEQ ID No: 13), and
   wherein QTL3 is located on chromosome 4 between marker BO02418 (SEQ ID No: 11) and BO01995 (SEQ ID No: 12) and is linked to marker BO02117 (SEQ ID No: 8).

9. The progeny plant as claimed in claim 8, wherein the progeny plant is resistant to *Plasmodiophora brassicae*.

10. A propagation material derived from a plant as claimed in claim 1, wherein the propagation material comprises the genetic determinant as defined in claim 1.

11. A propagation material capable of growing into a plant as claimed in claim 1.

12. The propagation material as claimed in claim 10, wherein the propagation material comprises a microspore, pollen, ovary, ovule, embryo, embryo sac, egg cell, cutting, root, root tip, hypocotyl, cotyledon, stem, leafs, flower, anther, seed, meristematic cell, protoplast or cell.

13. A tissue culture of propagation material as claimed in claim 10.

14. A harvested part of a *Brassica oleracea* plant as claimed in claim 1, which is selected from the group consisting of cabbage head, curd, stem, leaf, sprout, and seed, optionally in processed form, wherein the harvested part comprises the genetic determinant as defined in claim 1.

15. The harvested part as claimed in claim 14, wherein the harvested part is a food product.

* * * * *